United States Patent [19]

Rueger et al.

[11] Patent Number: 5,610,021

[45] Date of Patent: Mar. 11, 1997

[54] COMPOSITIONS AND METHODS FOR IDENTIFICATION AND USE OF SOLUBLE COMPLEX FORMS OF OSTEOGENIC PROTEINS

[75] Inventors: David C. Rueger, Hopkinton; William K. Jones, Brookline; Ronald F. Tucker, Holliston; Hermann Oppermann, Medway; Engin Ozkaynak, Milford; Kuber T. Sampath, Medway, all of Mass.

[73] Assignee: Creative BioMolecules, Inc., Hopkinton, Mass.

[21] Appl. No.: 206,864

[22] Filed: Mar. 4, 1994

Related U.S. Application Data

[63] Continuation-in-part of Ser. No. 27,070, Mar. 4, 1993, abandoned, which is a continuation-in-part of Ser. No. 841,646, Feb. 21, 1992, Pat. No. 5,266,683.

[51] Int. Cl.$^6$ .................. G01N 33/53; G01N 33/541; G01N 33/68; C07K 16/18
[52] U.S. Cl. .................. 435/7.2; 435/71; 435/7.92; 435/7.94; 530/350; 530/387.1; 530/388.85; 530/387.9; 530/388.1; 530/389.1
[58] Field of Search .................. 530/550, 387.1, 530/387.9, 388.1, 388.21, 389.1, 388.24, 388.25, 388.85; 435/7.2, 7.1, 7.92, 7.94

[56] References Cited

U.S. PATENT DOCUMENTS 5,468,845  11/1995  Opperman et al. .................. 530/387.9

FOREIGN PATENT DOCUMENTS

| 9011366 | 10/1990 | WIPO . |
| WO92/15323 | 9/1992 | WIPO . |
| WO93/00049 | 1/1993 | WIPO . |
| WO93/15197 | 8/1993 | WIPO . |
| WO94/03600 | 2/1994 | WIPO . |

OTHER PUBLICATIONS

Mawer, P. H. et al., Meth in Enzymology, 70:49–70, 1980.
Sevier, E. D. et al, Clin Chem, 27(11):1797–1805, 1981.
Ozkaynab, E et al, Embo Journal, 9(7):2085–2093, 1990.
Celeste, A. J. et al, PNAS, 87:9843–9847, Dec. 1990.
Doctor et al., "Sequencing, Biochemical Characterization, and Developmental Expression of a New Member of the TGF-β Superfamily in *Drosophila melanogaster*", *Developmental Biology*, 151:491–505 (1992).
Sauermann et al., "Cloning of a Novel TGF-β Related Cytokine, the vgr, From Rat Brain: Cloning of and Comparison to Homologous Human Cytokines", *Journal of Neuroscience Research*, 33:142–147 (1992).
Rosen et al., "The BMP proteins in bone formation and repair", *Reviews*, 8:97–102 (1992).
Wang et al., "Recombinant Human Bone Morphogenetic Protein Induces Bone Formation" *Proc. Natl. Acad. Sci.* 87:2220–2224 (1990).

*Primary Examiner*—Susan A. Loring
*Attorney, Agent, or Firm*—Testa, Hurwitz & Thibeault, LLP

[57] ABSTRACT

Disclosed are novel compositions of osteogenic proteins constituting soluble forms of these proteins, and methods and compositions for distinguishing between soluble and mature forms of these proteins.

30 Claims, 2 Drawing Sheets

```
OP-2:  RAPR SQQPFVVTFFRASPSPIRTPRAVRPLRRQPKKSNELPQANRLPGIFDDVHGSHGRQVC
OP-1:                          RSIR STGSKQRSQNRSKTPKNQEALRMANVAENSSSDQRQAC
Vgr-1:                         RTTR SASSRRRQQSRNRSTQSQDVSRGSGSSDYNGSELKTAC
BMP-5:                         RSVR AANKRKNQNRNKSSHQDSSRMSSVGDYNTSEQKQAC
60A:                    RSKR SASHPRKRKKSVSPNNVPLLEPMESTRSC
DPP:                    RSIR DVSGGEGGGKGGRNKRHARRPTRRKNHDDTC
BMP-2:    RHVRISR SLHQDEHSWSQIRPLLVTFGHDGKGHPLHK--REKR QAKH--KQRKRLKSSC
BMP-4:    RISR SLPQGSGNWAQLRPLLVTFGHDGRGHALTRRR RAKR SPKHHSQRARKKNKNC
Vg-1:                                                  RCKR PRRKR SYSKLPFTASNIC
BMP-3: RKKR STGVLLPLQ..............KSKNKKKQRKGPHRKSQTLQFDEQTLKKARRKQWIEPRNC
```

Fig. 2

COMPOSITIONS AND METHODS FOR IDENTIFICATION AND USE OF SOLUBLE COMPLEX FORMS OF OSTEOGENIC PROTEINS

RELATION TO RELATED APPLICATION

This application is a continuation-in-part of U.S. Ser. No. 08/027,070, filed Mar. 4, 1993, now abandoned, which is a continuation-in-part of U.S. Ser. No. 07/841,646, filed Feb. 21, 1992, now U.S. Pat. No. 5,266,683, the disclosures of which are incorporated herein by reference.

FIELD OF THE INVENTION

The present invention relates generally to osteogenic proteins and, more particularly, to methods and compositions for their production and purification.

BACKGROUND OF THE INVENTION

Osteogenic proteins are well known and described in the art. See, for example, U.S. Pat. Nos. 4,968,590; 5,011,691; 5,018,753 and 5,266,683, as well as various scholarly articles published in the scientific literature. See, for example, Ozkaynak et al. (1990) *EMBO J* 9:2085–2093; Ozkaynak et al. (1992), *J.Biol. Chem.* 267:13198–13205; Sampath et al. (1993) *PNAS* 90: 6004–6008; Wozney et al. (1988) *Science* 242: 1528–1534; Wang et al. (1988) *PNAS* 85:9484–9488; Wang et al. (1990) *PNAS* 87:2220–2224, and Celeste, et al. (1990) *PNAS* 87:9843–9847. The art has described how to isolate osteogenic proteins from bone and how to identify genes encoding these protein and express them using recombinant DNA technology.

The proteins that define the class of true osteogenic proteins constitute a group of proteins sharing a number of conserved structural characteristics. Each protein, on its own, can induce endochondral bone formation in a mammal when properly folded, dimerized and disulfide bonded to produce a dimeric species having the appropriate three dimensional conformation, and without requiring the addition of other osteogenic or non-osteogenic proteins. Typically, osteogenic proteins are provided to a site for bone induction in a mammal in association with a suitable matrix having the appropriate conformation to allow the infiltration, proliferation and differentiation of migrating progenitor cells. The construct of osteogenic protein adsorbed to the surfaces of a suitable matrix is generally referred to in the art as an osteogenic device. The proteins can be isolated from bone or, preferably, the gene encoding the protein is produced recombinantly in a suitable host cell. Methods for the production of osteogenic proteins and formulations of osteogenic devices are described in detail in the art. See, for example, U.S. Pat. Nos. 5,011,691, or 5,266,683, the disclosures of which are incorporated hereinabove by reference.

Improved methods for the recombinant expression of osteogenic proteins is an ongoing effort in the art. It is an object of this invention to provide an improvement in the methods for producing and purifying osteogenic proteins having high specific activity, and for formulating osteogenic devices comprising these proteins. Still another object is to provide means for distinguishing between the soluble form of the protein and the mature osteogenic protein species typically utilized in formulating osteogenic devices, and to provide polyclonal and monoclonal antibodies capable of distinguishing between these various species. Another object is to provide methods for producing antibodies which can recognize both forms of the protein. Still another object is to provide methods for monitoring each and all these forms of the protein in a fluid, including serum and production media. U.S. Pat. No. 4,857,956 and Urist et al. (1984) *Proc. Exp. Bio. Med.* 176: 472–475, describe a serum assay for detecting a protein purported to have osteogenic activity. The protein is not a member of the family of osteogenic proteins described herein, differing in molecular weight, structural characteristics and solubility from these proteins.

SUMMARY OF THE INVENTION

It has now been discovered that osteogenic protein as defined herein below, when secreted into cultured medium from mammalian cells contains as a significant fraction of the secreted protein a soluble form of the protein, and that this soluble form comprises the mature dimeric species, including truncated forms thereof, noncovalently associated with at least one, and preferably two pro domains. It further has been discovered that binding partners having specific binding affinity for an epitope on an osteogenic protein or precursor polypeptide chain can be used to discriminate between these two forms of the protein. Preferably the binding partner is a protein. In one preferred embodiment the binding protein is an antibody, which may be monoclonal, polyclonal or biosynthetically produced. These binding partners may be used as part of a purification scheme to selectively isolate the mature or the soluble form of the protein, as well as to quantitate the amount of mature and soluble forms produced. The antibodies may be used as part of a production protocol to monitor the pharmacological purity of an osteogenic protein preparation for therapeutic or other clinical applications. Specifically, a method now is provided herein to ensure that only one desired form of a protein is present in a composition. In addition, binding partners can be produced which recognize both protein forms and which may be used to advantage to monitor the quantity of total protein in solution. These binding partners also may be used as part of diagnostic treatments to monitor the concentration of osteogenic protein in solution in a body and to detect fluctuations in the concentration of the proteins in their various forms.

The foregoing and other objects, features and advantages of the present invention will be made more apparent from the following detailed description of the invention.

DETAILED DESCRIPTION

A soluble form of true osteogenic proteins now has been discovered wherein the protein consists essentially of the amino acid sequence of the protein. The soluble form is a non-covalently associated complex comprising the pro domain or a fragment thereof, noncovalently associated or complexed with a dimeric protein species having osteogenic activity, each polypeptide of the dimer having less than 200 amino acids and comprising at least the C-terminal six, and preferably seven cysteine skeleton defined by residues 335–431 and 330–431, respectively, of Seq. ID No. 1. Preferably, the polypeptide chains of the dimeric species comprise the mature forms of these sequences, or truncated forms thereof. Preferred truncated forms comprise the intact C-terminal domain and at least 10 amino acids of the N-terminal extension sequence e.g., preferably at least the sequence defined by residues 320–330 of Seq. ID 1. The soluble forms of these osteogenic proteins may be isolated from cultured cell medium, a mammalian body fluid, or may be formulated in vitro.

In vivo, under physiological conditions, the pro domain may serve to enhance the transportability of the proteins, and/or to protect the proteins from proteases and scavenger molecules, including antibodies. The pro domains also may aid in targeting the proteins to tissue, e.g., to bone.

The proteins contemplated by the invention and referred to herein as "osteogenic proteins" are true osteogenic proteins capable, on their own, of inducing endochondral bone formation when implanted in a mammal in association with a matrix. Without requiring the addition of other osteogenic or non-osteogenic proteins. A detailed description of these proteins appears, for example, in U.S. Pat. Nos. 4968,590, 5,011,691 and U.S. Ser. No. 841,646, and includes references to various members of the protein family identified to date. These family members include OP1, OP2, and the proteins referred to in the art as "bone morphogenic proteins": BMP2, BMP3, BMP4, BMP5, BMP6 and BMP9, as well as various known species variants, including Vgr, Vgl, 60A and DPP, and biosynthetic osteogenic constructs, including COP1, 3, 5, 7 and 16.

Figure 1:
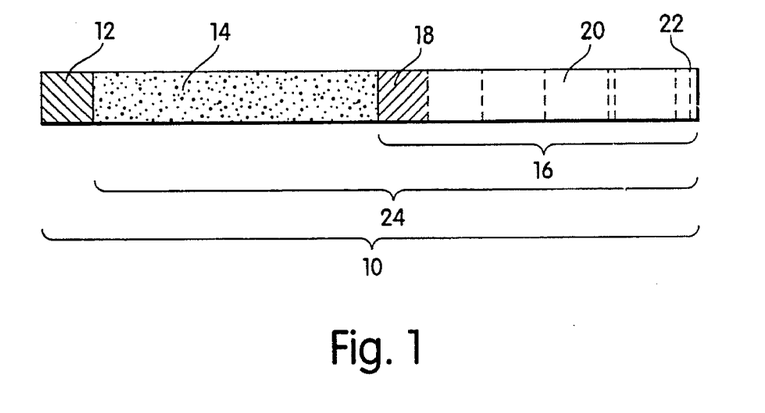
FIG. 1 is a schematic representation of an osteogenic protein polypeptide chain as expressed from a nucleic acid encoding the sequence, wherein the cross-hatched region represents the signal sequence; the stippled region represents the pro domain; the hatched region represents the N-terminus ("N-terminal extension") of the mature protein sequence; and the open region represents the C-terminal region of the mature protein sequence defining the conserved seven cysteine domain, the conserved cysteines being indicated by vertical hatched lines.
Figure 2:
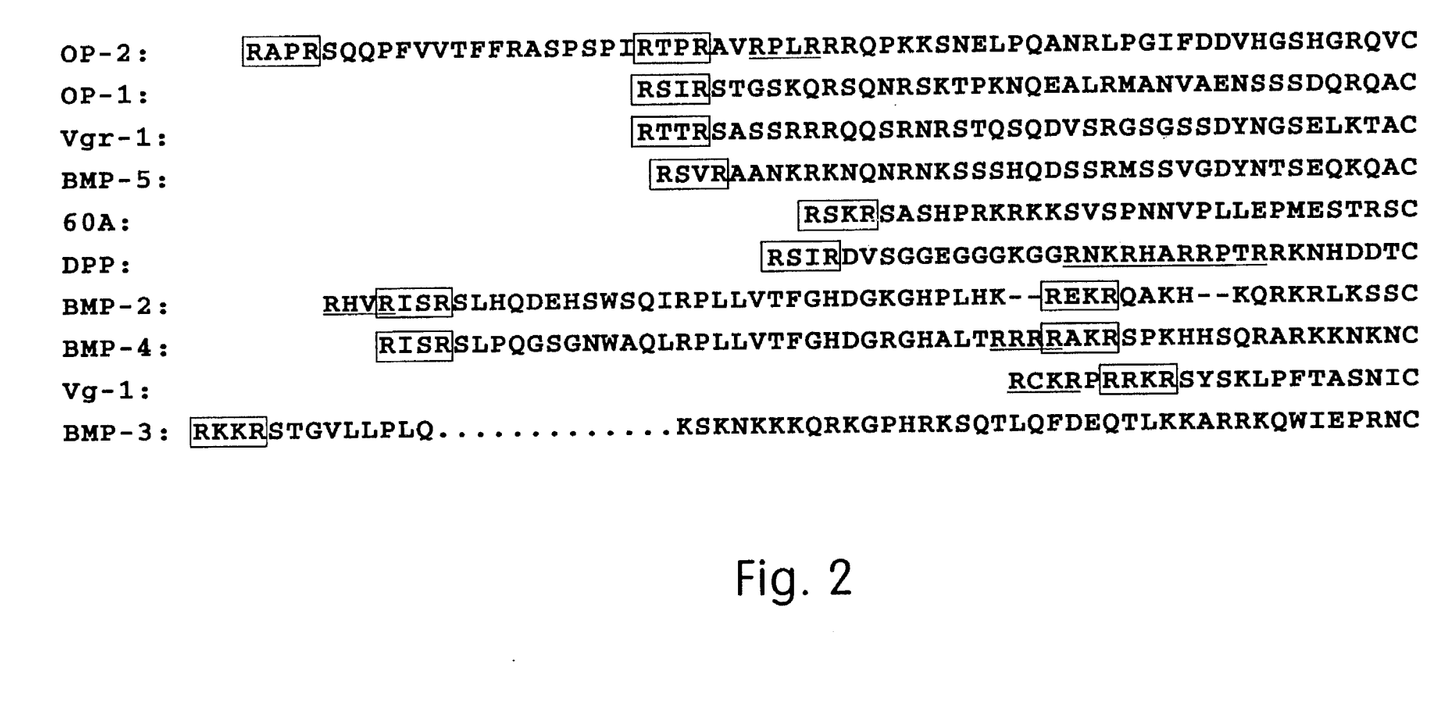
FIG. 2 lists the sequences of the N-terminal extensions of the mature forms of various osteogenic proteins.

The members of this family of proteins, which are a subclass of the TGF-β super-family of proteins, share characteristic structural features, represented schematically in FIG. 1, as well as substantial amino acid sequence homology in their C-terminal domains, including a conserved seven cysteine structure. As illustrated in the figure, the proteins are translated as a precursor polypeptide sequence 10, having an N-terminal signal peptide sequence 120, (the "pre pro" region, indicated in the figure by cross-hatching), typically less than about 30 residues, followed by a "pro" region 14, indicated in the figure by stippling, and which is cleaved to yield the mature sequence 16. The mature sequence comprises both the conserved C-terminal seven cysteine domain 20, and an N-terminal sequence 18, referred to herein as an N-terminal extension, and which varies significantly in sequence between the various osteogenic proteins. Cysteines are represented in the figure by vertical hatched lines 22. The polypeptide chains dimerize and these dimers typically are stabilized by at least one interchain disulfide bond linking the two polypeptide chain subunits. The mature subunits produced from mammalian cells typically have molecular weights in the range of about 15–23 kD, depending on the degree of glycosylation and N-terminal truncation. The dimeric species then typically have a molecular weight in the range of about 30–40 kD.

The signal peptide is cleaved during or soon after translation, at a cleavage site that can be predicted in a given sequence using the method of Von Heijne ((1986) *Nucleic Acids Research* 14:4683–4691.) The "pro" form of the protein subunit, 24, in FIG. 1, includes both the pro domain and the mature domain, peptide bonded together. Typically, this pro form is cleaved while the protein is still within the cell, and the pro domain remains noncovalently associated with the mature form of the subunit to form a soluble species that appears to be the primary form secreted from cultured mammalian cells. Typically, previous purification techniques utilized denaturing conditions that disassociated the complex.

Other soluble forms of osteogenic proteins secreted from mammalian cells include dimers of the pro forms of these proteins, wherein the pro domain is not cleaved from the mature domain, and "hemi-dimers", wherein one subunit comprises a pro form of the polypeptide chain subunit and the other subunit comprises the cleaved mature form of the polypeptide chain subunit (including truncated forms thereof), preferably noncovalently associated with a cleaved pro domain.

The isolated pro domain typically has regions of hydrophobicity, as determined both by analysis of the sequence and by characterization of its properties in solution. The isolated pro domains alone typically are not fully soluble in aqueous solutions. Accordingly, without being limited to any given theory, the non-covalent association of the cleaved pro domains with the mature osteogenic protein dimeric species may involve interaction of a hydrophobic portion of a given pro domain with a corresponding hydrophobic region on the dimeric species, the interaction of which effectively protects or "hides" an otherwise exposed hydrophobic region of the mature dimer from exposure to aqueous environments, enhancing the affinity of the mature dimer species for aqueous solutions.

Like the osteogenic proteins described herein, TGF-β also has a pro domain which associates non-covalently with the mature TGF-β protein form. However, unlike the osteogenic proteins described herein, the TGF-β pro domain contains numerous cysteines and forms disulfide bonds with a specific binding protein. The TGF-β1 pro domain also is phosphorylated at one or more mannose residues, while the osteogenic protein pro domains typically are not.

As described above, the active form of osteogenic protein, exemplified herein below by OP-1, is known to comprise a dimeric species composed of the mature sequence (e.g., amino acids 293–431 of Seq. ID NO. 1) or a truncated form thereof, appropriately disulfide bonded to produce an osteogenic dimeric species. These osteogenic proteins, in their mature forms, are neutral to basic proteins (e.g., pI in the range of about 7 to 8) and are, to varying degrees, relatively insoluble under physiological conditions. It now has been discovered that these proteins are secreted from mammalian cells in a soluble form and that this form comprises the mature dimeric species (also referred to herein as the "purified species") associated non-covalently with one or more copies of the pro domain. This form of the protein likely is the form which is present in the bloodstream. Unlike the latent form of TGF-β, this form of osteogenic protein does not inhibit activity. The soluble form itself may be active or, it may dissociate to release the mature dimeric species when the protein has arrived at a target tissue, such as bone tissue.

Thus antibodies now may be generated which recognize an osteogenic protein of interest, and these antibodies then used to monitor culture medium or endogenous levels of osteogenic protein in a body fluid, such as serum, whole blood or peritoneal fluid. Preferably, the antibody has binding specificity for the soluble form. Such antibodies may be generated by using the pro domain or a portion thereof as the antigen, or, preferably, the soluble complex itself. The pro domain may be preferably obtained by isolating the soluble complex and then separating the non-covalently associated pro domain from the mature domain using standard procedures, e.g., by separating the complex components by chromatographic means, preferably by ion-exchange chromatography in the presence of a denaturant, e.g., 6M urea. Alternatively, the pro protein in its monomeric form may be used as the antigen and the candidate antibodies screened by western blot or other standard immunoassay for those which recognize the pro form or soluble form of the protein of interest, but not the mature form. Where antibody capable of identifying both soluble and mature forms of the protein is desired, the complex itself preferably is used as the antigen source. Details of antibody production and exemplary immunoassays are provided below. Also provided is an example for detecting soluble osteogenic protein in a body fluid sample. The proteins contemplated to be useful in the methods and compositions of the invention include forms having varying glycosylation patterns and varying N-termini. They may be naturally occurring or biosynthetically derived, and may be produced by expression of recombinant DNA in procaryotic or eucaryotic host cells. The proteins are active as a single species (e.g., as homodimers), or combined as a mixed species. Useful sequences and eucaryotic and procaryotic expression systems are well described in the art. See, for example, U.S. Pat. Nos. 5,061,911 and 5,266,683 for useful expression systems. Useful sequences are recited in U.S. Pat. Nos. 4,968,590; 5,011,691; 5,018,753 and 5,266,683, and Ozkaynak et al. (1990) *EMBO J* 9:2085–2093; Ozkaynak et al., *J.Biol. Chem.* 267:13198–13205; Sampath et al. (1993) *PNAS* 90: 6004–6008; Wozney et al. (1988) *Science* 242: 1528–1534; Wang et al. (1988) *PNAS* 85:9484–9488; Wang et al. (1990) *PNAS* 87:2220–2224, Celeste, et al. (1990) *PNAS* 87:9843–9847 Weeks et al. (1987) *Cell* 51:861–867; Padgett, et al. (1987) *Nature* 325 81–84; Wharton et al. (1991) *PNAS* 88:9214–9218; Lyons et al. (1989) *PNAS* 86:4554–4558 and PCT international application WO93/00432 for OP1, OP2, DPP, 60A, Vg1, Vgr-1 and the BMP-2-6, and BMP-9 proteins. Accordingly, these proteins, including allelic, species and other naturally-occurring and biosynthetic sequence variants thereof are contemplated to be useful in the inteant application. Other useful sequences include biosynthetic constructs including, without limitation any of the sequences referred to in U.S. Pat. No. 5,011,691 as COP-1, -3, -5, -7, -16; and chimeric constructs created by combining sequences from two or more different osteogenic proteins. As will be appreciated by those having ordinary skill in the art, chimeric constructs readily can be created using standard molecular biology and mutagenesis techniques combining various portions of different osteogenic sequences to create a novel sequence, and these forms of the protein also are contemplated herein.

A particularly preferred embodiment of the proteins contemplated by the invention includes proteins whose amino acid sequence in the cysteine-rich C-terminal domain has greater than 60% identity, and preferably greater than 65% identity with the amino acid sequence of OPS (e.g., residues 335–431 of Seq. ID No. 1).

In another preferred aspect, the invention contemplates osteogenic proteins comprising species of polypeptide chains having the generic amino acid sequence herein referred to as "OPX" which accommodates the homologies between the various identified species of the osteogenic OP1 and OP2 proteins, and which is described by the amino acid sequence presented below and in Sequence ID No. 5.

| Cys 1 | Xaa | Xaa | His | Glu 5 | Leu | Tyr | Val | Ser | Phe 10 |
|---|---|---|---|---|---|---|---|---|---|
| Xaa | Asp | Leu | Gly | Trp 15 | Xaa | Asp | Trp | Xaa | Ile 20 |
| Ala | Pro | Xaa | Gly | Tyr 25 | Xaa | Ala | Tyr | Tyr | Cys 30 |
| Glu | Gly | Glu | Cys | Xaa 35 | Phe | Pro | Leu | Xaa | Cys 40 |
| Xaa | Met | Asn | Ala | Thr 45 | Asn | His | Ala | Ile | Xaa 50 |
| Gln | Xaa | Leu | Val | His 55 | Xaa | Xaa | Xaa | Pro | Xaa 60 |
| Xaa | Val | Pro | Lys | Xaa 65 | Cys | Cys | Ala | Pro | Thr 70 |
| Xaa | Leu | Xaa | Ala | Xaa 75 | Ser | Val | Leu | Tyr | Xaa 80 |
| Asp | Xaa | Ser | Xaa | Asn 85 | Val | Ile | Leu | Xaa | Lys 90 |
| Xaa | Arg | Asn | Met | Val 95 | Val | Xaa | Ala | Cys | Gly 100 |
| Cys | His, | | | | | | | | | and wherein Xaa at res. 2=(Lys or Arg); Xaa at res. 3=(Lys or Arg); Xaa at res. 11=(Arg or Gln); Xaa at res. 16=(Gln or Leu); Xaa at res. 19=(Ile or Val); Xaa at res. 23=(Glu or Gln); Xaa at res. 26 =(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn);. Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 97=(Arg or Lys).

In still another preferred aspect, the invention contemplates osteogenic proteins encoded by nucleic acids which hybridize to DNA or RNA sequences encoding the C-terminal seven cysteine domain of OP1 or OP2 under stringent hybridization conditions. As used herein, stringent hybridization conditions are defined as hybridization in 40% formamide, 5×SSPE, 5×Denhardt's Solution, and 0.1% SDS at 37° C. overnight, and washing in 0.1×SSPE, 0.1% SDS at 50° C. (See, for example, *Molecular Cloning: A Laboratory Manual*, Maniatis et al., eds. 2d. ed., Cold Spring Harbor Press, Cold Spring Harbor, 1989.)

Useful pro domains include the full length pro domains described below, as well as various truncated forms hereof, particularly truncated forms cleaved at proteolytic Arg-Xaa-Xaa-Arg cleavage sites. For example, in OP-1, possible pro sequences include sequences defined by residues 30–292 (full length form); 48–292; and 158–292. Soluble OP-1 complex stability is enhanced when the pro domain comprises the full length form rather than a truncated form, such as the 48–292 truncated form, in that residues 30–47 show sequence homology to the N-terminal portions of other osteogenic proteins, and are believed to have particular utility in enhancing complex stability for all osteongeic proteins. Accordingly, currently preferred pro sequences are those encoding the full length form of the pro domain for a given morphogen (see below). Other pro sequences contemplated to have utility include biosynthetic pro sequences, particularly those that incorporate a sequence derived from the N-terminal portion of one or more osteogenic protein pro sequences.

A brief description of OP-1 is described below, followed by examples disclosing how to isolate soluble forms of these proteins and how to generate and identify antibodies having specificity for the mature or "purified" form, and the soluble or "media" form, or for both forms of proteins. In a particularly preferred embodiment, antibodies, or other binding proteins which recognize the soluble form of the protein do not also recognize the precursor form of the pro domain peptide alone. As will be appreciated by those having ordinary skill in the art, with this disclosure it is possible to more accurately identify and/or quantitate the amount of a given, preferred form of a recombinantly produced osteogenic protein present in the culture media, than by previously available methods, e.g., methods which relied on antibody specific for epitopes present only on the mature form or soluble form of the protein. It also now is possible to accurately isolate a desired form of the protein. For example, one can preferentially isolate the soluble complex form by passing the culture media over an affinity column that has bound antibody with binding specificity only for the pro domain form, and then selectively desorbing the bound protein using standard procedures to modify binding conditions, thereby allowing selective isolation of the complex. For example, one can modify binding conditions by using low pH, denaturants, or by competition with a peptide specific for the antibody binding site. It also is anticipated that the antibodies and protocols can be used to identify both forms of the protein in a solution. A particularly useful application of the invention is as part of a protocol for monitoring the pharmacological purity of an osteogenic protein composition to be used for clinical applications.

While the examples demonstrate the utility of the invention by means of an illustrative protein, OP1, it is intended to be understood that the methods and compositions taught herein can be extended without undue experimentation to other members of the family of osteogenic proteins. Similarly, while the examples are directed to antibodies as the binding partner having specificity for an epitope on an osteogenic protein, and immunoassays as the detection protocols, any binding partner, particularly any binding protein capable of providing the same discriminatory power as the antibodies described herein are contemplated. Moreover, while only monoclonal and polyclonal antibodies are described in detail, other antibody forms, including biosynthetics such as single chain constructs, referred to in the art as "sFv's" also are contemplated to be within the scope of the invention.

OP1—Refers generically to the family of osteogenically active proteins produced by expression of part or all of the hOP1 gene. Also referred to herein and in related applications as "OPI" and "OP-1".

hOP1-PP—Amino acid sequence of human OP1 protein (prepro form), Seq. ID No. 1, residues 1–431. Also referred to in related applications as "OP1-PP" and "OPP".

OP1-18Ser—Amino acid sequence of mature human OP1 protein, Seq. ID No. 1, residues 293–431. N-terminal amino acid is serine. Originally identified as migrating at 18 kDa on SDS-PAGE in COS cells. Depending on protein glycosylation pattern in different host cells, also migrates at 23 kDa, 19 kDa and 17 kDa on SDS-PAGE. Also referred to in related applications as "OP1-18".

OPS—Amino acid sequence defining the C-terminal six cysteine domain, residues 335–431 of Seq. ID No. 1.

OP7—Amino acid equence defining the C-terminal seven cysteine domain, residues 330–431 of Seq. ID No. 1.

I. Physical and Antigenic Structure of Soluble OP-1 and Mature, Dimeric OP-1

1a. Solubility of Mature, Dimeric OP-1

The solubility properties of purified mature OP-1 dimers (also referred to herein as "pure OP-1" or "purified OP-1" in contrast to OP-1 as found in media, also referred to herein as soluble or "media" OP-1) have been extensively studied. The conclusion of these studies has been that mature OP-1 is soluble typically only under denaturing conditions. In contrast, the recombinantly produced OP-1 initially secreted into mammalian cell (CHO cell) conditioned media remains soluble in the absence of denaturants. Mature OP-1 has been shown to be soluble in low concentrations of detergents including 0.1% SDS and CHAPS, and in mild denaturing conditions such as low ionic strength at low pH, or in the presence of denaturants with non-ionic detergents, e.g., 6M urea +0.3% Tween-80, and in the presence of acidified organic solvent like 50% acetonitrile with 0.1% TFA. It has now been discovered that denaturing solvent conditions separate the pro domain from the mature region, and that previously developed purification protocols involving denaturants prohibit isolation of the complexed, highly soluble form. As disclosed below, purification of the soluble complexes must be done in the absence of denaturing conditions.

1.b Production of Secreted OP-1 by CHO Cells

Mammalian cell produced OP-1 is synthesized and secreted in a soluble dimeric form, as a result of several post-translational modifications, including appropriate folding, dimerization, glycosylation and cleavage at the juncture of the pro domain and mature domain. Some pro-OP-1 also is secreted without being cleaved, resulting in secreted pro OP-1.

1.c Identification of Soluble OP-1 (complexed)

Recombinant OP-1 as expressed by CHO (Chinese hamster ovary cells, see U.S. Patent No. 5,266,638 for exemplary protocol) is secreted into serum containing media and exists as in a soluble form. This apparent solubility of OP-1 could be caused by the association of OP-1 with a component of the serum or by the secretion of OP-1 from CHO cells in a more soluble form than its final purified state.

1.d Cleveland Mapping of the 39 kDa Protein

Using metabolically labelled protein, a methionine-labeled 39 kDa protein from cultured media co-precipitates in an OP-1-dependent manner with OP-1. Protein was further characterized by Cleveland mapping using standard methodologies (see, for example Cleveland, D. W. (1977) *J. Biol. Chem.* 252:1102). Bands having an apparent molecular weight of 50, 39 and 19/17 kDa-based on comparison with standard molecular weight markers, were isolated from a PAGE gel, the gel slices placed in the wells of a 20% acrylamide gel along with various amounts of endoproteinase lys-C, electrophoresed into the stacking gel and allowed to digest for 30 min. followed by resolving the generated fragments on the 20% gel. The 50 kDa protein was cleaved to yield two fragments. The larger of these was also generated by the 39 kDa protein while the smaller was generated by the 19/17 kDa proteins. This evidence strongly suggested that the 39 kDa protein was the pro domain of OP-1. Further analysis of the secreted form of OP-1 was made possible by the isolation of mature OP-1 as a soluble complex from CHO conditioned media.

2. Purification Protocol for Soluble Osteogenic Protein

Soluble complexes comprising osteogenic protein can be isolated from conditioned media using a simple, three step chromatographic protocol performed in the absence of denaturants. The protocol involves running the media (or body fluid) over an affinity column, followed by ion exchange and gel filtration chromatographies. The affinity column described below is a Zn-IMAC column. An alternative protocol also envisioned to have utility is an immunoaffinity column, created using standard procedures and, for example, using antibody specific for a given osteogenic protein pro domain (complexed, for example, to a protein A-conjugated Sepharose column.) Protocols for developing immunoaffinity columns are well described in the art, (see, for example, *Guide to Protein Purification*, M. Deutscher, ed., Academic Press, San Diego, 1990, particularly sections VII and XI.)

In this experiment OP-1 was expressed in CHO cells as described above. The CHO cell conditioned media containing 0.5% FBS was initially purified using Immobilized Metal-Ion Affinity Chromatography (IMAC). The soluble OP-1 complex from conditioned media binds very selectively to the Zn-IMAC resin, presumably through association with the pro domain, and a high concentration of imidazole (50 mM imidazole, pH 8.0) is required for the effective elution of the bound complex. The Zn-IMAC step separates the soluble OP-1 from the bulk of the contaminating serum proteins that elute in the flow through and 35 mM imidazole wash fractions. The Zn-IMAC purified soluble OP-1 is next applied to an S-Sepharose cation-exchange column equilibrated in 20 mM $NaPO_4$ (pH 7.0) with 50 mM NaCl. This S-Sepharose step serves to further purify and concentrate the soluble OP-1 complex in preparation for the following gel filtration step. The protein was applied to a Sephacryl S-200HR column equilibrated in TBS. Using substantially the same protocol, soluble osteogenic proteins also may be isolated from one or more body fluids, including serum, cerebro-spinal fluid or peritoneal fluid.

IMAC was performed using Chelating-Sepharose (Pharmacia) that had been charged with three column volumes of 0.2M $ZnSO_4$. The conditioned media was titrated to pH 7.0 and applied directly to the ZN-IMAC resin equilibrated in 20 mM HEPES (pH 7.0) with 500 mM NaCl. The Zn-IMAC resin was loaded with 80 mL of starting conditioned media per mL of resin. After loading the column was washed with equilibration buffer and most of the contaminating proteins were eluted with 35 mM imidazole (pH 7.0) in equilibration buffer. The soluble OP-1 complex is then eluted with 50 mM imidazole (pH 8.0) in 20 mM HEPES and 500 mM NaCl.

The 50 mM imidazole eluate containing the soluble OP-1 complex was diluted with nine volumes of 20 mM $NaPO_4$ (pH 7.0) and applied to an S-Sepharose (Pharmacia) column equilibrated in 20 mM $NaPO_4$ (pH 7.0) with 50 mM NaCl. The S-Sepharose resin was loaded with an equivalent of 800 mL of starting conditioned media per mL of resin. After loading the S-Sepharose column was washed with equilibration buffer and eluted with 100 mM NaCl followed by 300 mM and 500 mM NaCl in 20 mM $NaPO_4$ (pH 7.0). The 300 mM NaCl pool was further purified using gel filtration chromatography. Fifty mls of the 300 mm NaCl eluate was applied to a 5.0×90 cm Sephacryl S-200HR (Pharmacia) equilibrated in Tris buffered saline (TBS), 50 mM Tris, 150 mM NaCl (pH 7.4). The column was eluted at a flow rate of 5 mL/minute collecting 10 mL fractions. The apparent molecular of the soluble OP-1 was determined by comparison to protein molecular weight standards (alcohol dehydrogenase (ADH, 150 kDa), bovine serum albumin (BSA, 68 kDa), carbonic anhydrase (CA, 30 kDa) and cytochrome C (cyt C, 12.5 kDa). (see FIG. 3) The purity of the S-200 column fractions was determined by separation on standard 15% polyacrylamide SDS gels stained with coomassie blue. The identity of the mature OP-1 and the pro-domain was determined by N-terminal sequence analysis after separation of the mature OP-1 from the pro-domain using standard reverse phase C18 HPLC.

Figure 3:
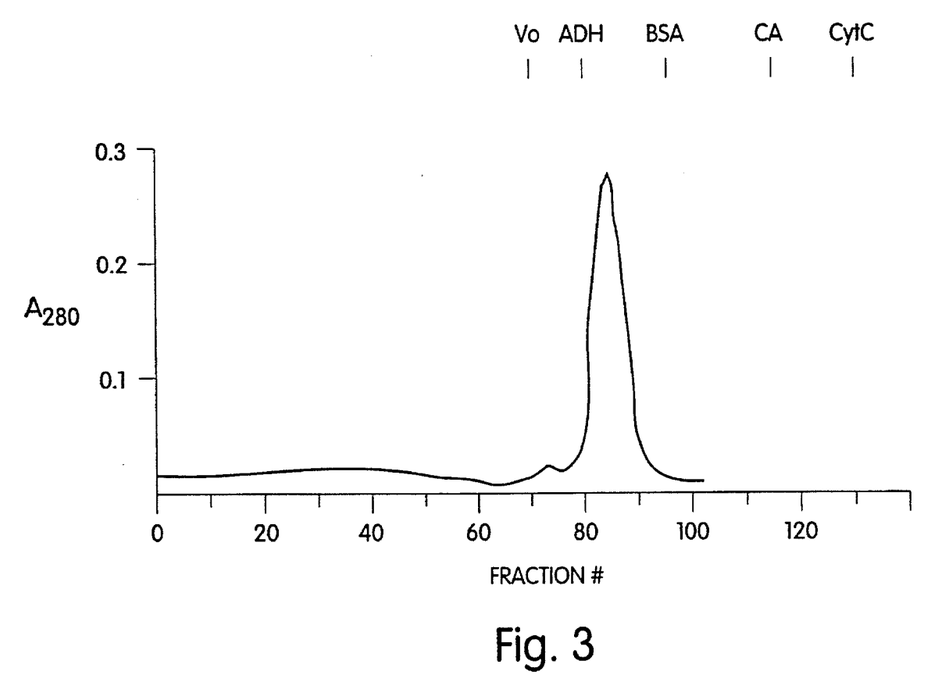
FIG. 3 is a gel filtration column elution profile of a soluble osteogenic protein (OP-1) produced and purified from a mammalian cell culture by IMAC, S-Sepharose and S-200HR chromatography in TBS (Tris-buffered saline), wherein $V_o$ is the void volume, ADH is alcohol dehydrogenase (MW 150 kDa), BSA is bovine serum albumin (MW 67 kDa), CA is carbonic anhydrase (MW 29 kDa) and CytC is cytochrome C (MW 12.5 kDa).

FIG. 3 shows the absorbance profile at 280 nm. The soluble OP-1 complex elutes with an apparent molecular weight of 110 kDa. This agrees well with the predicted composition of the soluble OP-1 complex with one mature OP-1 dimer (35–36 kDa) associated with two pro-domains (39 kDa each). Purity of the final complex can be verified by running the appropriate fraction in a reduced 15% polyacrylamide gel.

The complex components can be verified by running the complex-containing fraction from the S-200 or S-200HR columns over a reverse phase C18 HPLC column and eluting in an acetonitrile gradient (in 0.1% TFA), using standard procedures. The complex is dissociated by this step, and the pro domain and mature species elute as separate species. These separate species then can be subjected to N-terminal sequencing using standard procedures (see, for example, *Guide to Protein Purification*, M. Deutscher, ed., Academic Press, San Diego, 1990, particularly pp. 602–613), and the identity of the isolated 36 kD, 39 kDa proteins confirmed as mature osteogenic protein and isolated, cleaved pro domain, respectively. N-terminal sequencing of the isolated pro domain from mammalian cell produced OP-1 revealed 2 forms of the pro domain, the predominant form being the intact form (beginning at residue 30 of Seq. ID No. 1) and, as a minor species, a truncated form, (beginning at residue 48 of Seq. ID No. 1.) N-terminal sequencing of the polypeptide subunit of the isolated mature species reveals a range of N-termini for the mature sequence, beginning at residues 293, 300, 313, 315, 316, and 318, of Seq. ID No. 1, all of which are active as demonstrated by the standard bone induction assay. (See, for example, U.S. Pat. Nos. 5,011,691 and 5,266,683 for descriptions of the standard rat bone induction assay.)

II. Osteogenic Protein Detection

As indicated above, the method and compositions of the invention are directed to identifying and/or quantitative preferred forms of osteogenic protein in a solution, such as a culture medium or body fluid. As will be appreciated by those skilled in the art, any means for specifically identifying and quantifying the protein is contemplated. The current state of the art for identifying proteins in solution is by means of an immunoassay, wherein an antibody capable of binding specifically to the protein of interest is used to identify the protein in solution and the amount of bound complex formed then is determined.

Antibody methodologies are well understood and described in the literature. A more detailed description of their preparation can be found, for example, in *Practical Immunology*, Butt, W. R., ed., Marcel Dekker, New York, 1984. Broadly, antibodies may be raised against one or more preferred forms of an osteogenic protein by immunizing a suitable animal with an immunogenic preparation under conditions sufficient to induce antibody production in that animal. Monoclonal antibodies then can be obtained by fusing suitable antibody producing cells such as spleen or lymph node cells to myeloma cells and screening the fusion products for nuclear reactivity against the immunogen source (e.g., cell line or particular cell type determinant) using standard techniques.

The currently preferred method for detecting osteogenic proteins in a solution and/or for quantitating them is by detecting the proteins with osteogenic protein-specific antibodies. The antibodies may be monoclonal or polyclonal in origin, and may be produced by standard methodologies. The osteogenic proteins used as immunogens may be prepared as described above. That is, an intact dimeric species or soluble complex may be used as the antigen (immunogen). Alternatively, a pro domain peptide can be used to advantage, obtained for example, by dissociating a soluble complex and isolating the peptide, or by enzymatic digestion of a precursor form. Alternatively, the entire precursor form may be used as the immunogen.

Antibodies to one or more of these proteins then are raised using standard methods. The antibodies then are exposed to the fluid sample under conditions sufficient to allow specific binding of the antibody to its specific epitope, and the binding partner-ostegenic protein complex formed (here, antibody-ostegenic protein complex) then detected.

Immunoassay design considerations include preparation of antibodies (monoclonal or polyclonal) having sufficiently high binding specificity for their antigen that the specifically-bound antibody-antigen complex can be distinguished reliably from nonspecific interactions. The higher the antibody binding specificity, the lower the antigen concentration that can be detected. The choice of tagging label for detecting osteogenic protein-antibody complex formation also will depend on the detection limitations desired. Enzyme assays (ELISAs) typically allow detection of a colored product formed by interaction of the enzyme-tagged complex with an enzyme substrate. Alternative labels include radioactive or fluorescent labels. The most sensitive label known to date is a chemiluminescent tag where interaction with a reactant results in the production of light. Useful labels include chemiluminescent molecules such as acridium esters or chemiluminescent enzymes where the reactant is an enzyme substrate. When, for example, acridium esters are reacted with an alkaline peroxide solution, an intense flash of light is emitted, allowing the limit of detection to be increased 100 to 10,000 times over those provided by other labels. In addition, the reaction is rapid. A detailed review of chemiluminescence and immunoassays can be found in Weeks, et al., (1983) *Methods in Enzymology* 133:366–387. Other considerations include the use of microtiter wells or column immunoassays. Column assays may be particularly advantageous where rapidly reacting labels, such as chemiluminescent labels, are used. The tagged complex can be eluted to a post-column detector which also contains the reactant or enzyme substrate, allowing the subsequent product formed to be detected immediately.

A detailed review of immunological assay design, theory and protocols can be found in numerous texts in the art, including *Practical Immunology*, Butt, W. R., ed., Marcel Dekker, New York, 1984. Of the various immunoassay formats available, one of the most sensitive is the sandwich technique. In this method, two antibodies capable of binding the analyte of interest are used: one immobilized onto a solid support, and one free in solution, but labeled with some easily detectable chemical compound. As described above, examples of chemical labels that may be used for the second antibody include radioisotopes, fluorescent compounds, and enzymes or other molecules which generate colored or electrochemically active products when exposed to a reactant or enzyme substrate. When samples containing analyte (e.g., osteogenic protein in a given form) are placed in this system, the analyte binds to both the immobilized antibody and the labelled antibody. The result is a "sandwich" immune complex on the support's surface. The analyte is detected by washing away nonbound sample components and excess labeled antibody and measuring the amount of labeled antibody complexed to analyte on the support's surface. The sandwich immunoassay is highly specific and very sensitive, provided that labels with good limits of detection are used.

Another useful form of immunoassay, particularly useful for screening candidates is the Western blot. Here, proteins of interest are dispersed by gel electrophoresis and immobilized on a nitrocellulose membrane. Candidate antibodies then are added, typically complexed with a means for detection, e.g., radioactive label or enzyme as described above, and complex formation is allowed to occur. The membrane then is washed to remove proteins interacting only by non-specific binding interactions, and complexes that remain bound are detected. A detailed standard protocol is provided in *Molecular Cloning: A Laboratory Manual*, Sambrook et al., eds. 2d.ed., Cold Spring Harbor Press, Cold Spring Harbor, 1989. As used herein, typically, osteogenic proteins are electrophoresed under both reducing and oxidizing conditions.

2.a Antibody Production

Provided below are standard protocols for polyclonal and monoclonal antibody production. For antibodies which recognize the soluble complex form only, preferably the isolated complex itself is used as the antigen. Alternatively, the antigen may comprise the isolated pro domain or a peptide fragment thereof. Where antibodies specific to the mature protein are desired, the antigen preferably comprises the mature dimeric form (e.g., the "purified" form) or a subunit of the dimer comprising at least the C-terminal domain, or a peptide fragment thereof.

2a. Polyclonal Antibodies

Antibodies then are synthesized as described herein below, and tested in vitro for cross-reactivity with the various forms of the protein of interest.

Polyclonal antibody may be prepared as follows. Each rabbit is given a primary immunization of 100 ug/500 µl of antigen, 500 µl Complete Freund's Adjuvant. Solubility of a given antigen may be enhanced as needed by combining the antigen in a solubilizing agent, e.g., 0.1% SDS, prior to combination with the adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against the osteogenic protein antigen is detected in the serum using an ELISA assay. Then, the rabbit is boosted monthly with 100 µg of antigen and bled (15 ml per bleed) at days seven and ten after boosting.

2b. Monoclonal Antibodies.

Monoclonal antibody specific for a given osteogenic protein may be prepared as follows. A mouse is given two injections of the osteogenic protein antigen. The protein or protein fragment preferably is recombinantly produced. The first injection contains 100 µg of antigen in complete Freund's adjuvant and is given subcutaneously. The second injection contains 50 µg of antigen in incomplete adjuvant and is given intraperitoneally. The mouse then receives a total of 230 µg of OP-1 in four intraperitoneal injections at various times over an extended period of time (e.g., a one to eight month period.) One week prior to fusion, the mouse is boosted intraperitoneally with antigen (e.g., 100 μg) and may be additionally boosted with a peptide fragment conjugated to bovine serum albumin with a suitable cross linking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for mature or soluble osteogenic protein-specific antibodies using the appropriate portion of the osteogenic protein sequence as antigen. The cell fusion and monoclonal screening steps readily are performed according to standard procedures well described in standard texts widely available in the art.

2c. Antibody Specificity.

Using these standard procedures, anti-pro domain antisera was prepared from rabbits using the isolated pro domain from OP-1 as the antigen, and monoclonal antibody ("mAb") to the mature domain was produced in mice, using an *E. coli*-produced truncated form of OP-1 as antigen.

Standard Western blot analysis performed as described herein above under reducing conditions demonstrates that the anti-pro domain antisera ("anti-pro") is specific for the pro domain only, while the mAb to mature OP-1 ("anti-mature OP-1") is specific for the dimer subunits, that the two antibodies do not cross-react, and that the antibodies and can be used to distinguish between soluble and mature protein forms in a sample, e.g., of conditioned media or serum. A tabular representation of the Western blot results is in Table I below, where reactivity of mAb to mature OP-1 is indicated by "yy", and reactivity of the anti-pro antisera is indicated by "xx".

TABLE I

| Antibody | Purified Sol OP1 | Conditioned CHO Cell Media | Isolated Pro Domain | Purified Dimer Subunits |
|---|---|---|---|---|
| "anti-pro" | xx | xx | xx | |
| "anti-mature OP-1" | yy | yy | | yy |

In a second series, monoclonal antibodies were raised against each of the following antigens: soluble complex and uncomplexed, mature dimeric species.

Clones then were screened for reactivity against the various forms of OP-1, in an ELISA assay, as described above. Here, the various forms of OP1 tested were immobilized on a surface, the antibody to be screened then was added, and bound antibody detected using a goat anti-mouse antibody. Five different phenotypes or binding categories were identified and are described below. In the table, "S" means soluble complex; "M" means mature, dimeric species, and "P" means isolated pro domain.

TABLE II

| | Protein Form | | |
|---|---|---|---|
| | M | S | P |
| Category | | | |
| 1 | + | + | |
| 2 | | + | + |
| 3 | | + | |
| 4 | | | + |

TABLE II-continued

| | Protein Form | | |
|---|---|---|---|
| | M | S | P |
| Category | | | |
| 5 | + | | |

Antibodies having the binding character of category #1 recognize an epitope present on both the uncomplexed dimeric species and the soluble form.

Antibodies having the binding character of category #2 recognize an epitope present on both the soluble complex and the pro domain. Antibodies having the binding character of category #3 only recognize the soluble complex form, verifying that a conformational change occurs upon complex formation sufficient to create an epitope not present on other forms of the protein. Antibodies having this binding character are particularly useful for verifying the presence of a complex, including the formation of the soluble complex in vitro from its components (e.g., uncomplexed dimer and isolated pro domain peptide.)

Antibodies having the binding character of category #4 only recognize an epitope on the pro domain, verifying that complex formation is sufficient to mask or destroy an epitope present on the soluble complex. Similarly, antibodies having the binding character of category #5 only recognize an epitope on the mature, dimeric uncomplexed protein form, but not the soluble complex.

Of course, individual members within a given category may bind different epitopes. Accordingly, their binding character with respect to the different protein forms may vary depending on the assay conditions. For example, individual members of category #1, while still recognizing the mature and soluble forms, show preferentially binding affinity for the soluble form over the mature form under sandwich ELISA conditions where the member of category #1 constituted the capture antibody. Similarly, individual members of category #2 demonstrate variable binding for the pro domain under Western blot conditions.

III. Immunoassays

The ability to detect osteogenic proteins in solution and to distinguish between soluble and mature dimeric forms provides a valuable tool for protein production systems. Quality control considerations require that means be available for determining both the form of the protein in solution and its quantity. This is particularly true for biological therapeutics where pharmacologically certain forms must be provided for clinical use. The method also provides a useful tool for diagnostic assays, allowing one to monitor the level and type of osteogenic protein free in the body, e.g., in serum and other body fluids.

A currently preferred detection means for evaluating the level of osteogenic protein in a fluid, including culture or a body fluid, comprises an immunoassay utilizing an antibody or other suitable binding protein capable of reacting specifically with an osteogenic protein and being detected as part of a complex with the protein. Immunoassays may be performed using standard techniques known in the art and using antibodies raised against the protein and specific for that protein.

Antibodies which recognize an osteogenic protein form of interest may be generated as described herein and these antibodies then used to monitor the levels of protein in a fluid, including a body fluid, such as serum, whole blood or peritoneal fluid.

To monitor endogenous concentrations of the soluble form of the protein, the antibody chosen preferably has binding specificity for the soluble form. For endogenous proteins, these antibodies may have specificity for the pro domain and/or the soluble complex (e.g., binding categories 1–3, above). Such antibodies may be generated by using the pro domain or a portion thereof as the antigen, or the soluble complex itself, essentially as described herein. A suitable pro domain for use as an antigen may be obtained by isolating the soluble complex and then separating the non-covalently associated pro domain from the mature domain using standard procedures, e.g., by chromatographic means (preferably using an ion-exchange column under denaturing conditions, e.g., 6M urea), as described above or by separation by gel electrophoresis. Alternatively, the pro form of the protein in its monomeric form may be used as the antigen and the candidate antibodies screened by Western blot or other standard immunoassay for those which recognize the pro domain of the soluble form of the protein of interest, but not the mature form, also as described above.

Monomeric pro forms can be obtained from cell lysates of CHO produced cells, or from prokaryotic expression of a DNA encoding the pro form, in for example, *E.coli*, or from a commercially available bacculovirus expression system in insect cells. The pro form, which has an apparent molecular weight of about 50 kDa in mammalian cells, can then be isolated as described above.

In order to detect and/or quantitate the amount of osteogenic protein present in a solution, an immunoassay may be performed to detect the osteogenic protein using a polyclonal or monoclonal antibody specific for that protein. Here, soluble and mature forms of the osteogenic protein also may be distinguished by using antibodies that discriminate between the two forms of the proteins as described above. Currently preferred assays include ELISAS and radioimmunassays, including standard competitor assays useful for quantitating the osteogenic protein in a sample, where an unknown amount of sample protein is allowed to react with anti-osteogenic protein antibody and this interaction is competed with a known amount of labeled antigen. The level of bound or free labeled antigen at equilibrium then is measured to quantitate the amount of unlabeled antigen in solution, the amount of sample antigen being proportional to the amount of free labeled antigen. Exemplary protocols for these assays are provided below. However, as will be appreciated by those skilled in the art, variations of these protocols, as well as other immunoassays, including Western blots, are well known in the literature and within the skill of the art. For example, in the ELISA protocol provided below, soluble OP-1 is identified in a sample using biotinylated anti-pro antiserum. Biotinylated antibodies can be visualized in a colormetric assay or in a chemiluminescent assay, as described below. Alternatively, the antibody can be radio-labeled with a suitable molecule, such as $^{125}I$. Still another protocol that may be used is a solid phase immunoassay, preferably using an affinity column with anti-osteogenic protein antibody complexed to the matrix surface and over which a serum sample may be passed. A detailed description of useful immunoassays, including protocols and general considerations is provided in, for example, *Molecular Cloning: A Laboratory Manual*, Sambrook et al., eds. Cold Spring Harbor Press, New York, 1989, particularly Section 18.

For serum assays, the serum preferably first is partially purified to remove some of the excess, contaminating serum proteins, such as serum albumin. Preferably the serum is extracted by precipitation in ammonium sulfate (e.g., 45%) such that the complex is precipitated. Further purification can be achieved using purification strategies that take advantage of the differential solubility of soluble osteogenic protein complex or mature osteogenic proteins relative to that of the other proteins present in serum. Further purification also can be achieved by chromatographic techniques well known in the art.

3a. Assays

Soluble OP-1 may be detected using a polyclonal or monoclonal antibody in an ELISA, as described below in this experiment, polyclonal antibody specific for the OP-1 pro domain is omalyzedl μg/100 μl of affinity-purified polyclonal rabbit IgG specific for OP-1-pro is added to each well of a 96-well plate and incubated at 37° C. for an hour. The wells are washed four times with 0.167M sodium borate buffer with 0.15M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 μl aliquot of an appropriate dilution of each of the test samples of cell culture supernatant or serum sample is added to each well in triplicate and incubated at 37° C. for 30 min. After incubation, 100 μl biotinylated antibody from rabbit anti-pro anti-serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 μl strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 μl substrate (ELISA Amplification System Kit, Life Technologies, Inc., Bethesda, Md.) is added to each well incubated at room temperature for 15 min. Then, 50 μl amplifier (from the same amplification system kit) is added and incubated for another 15 min at room temperature. The reaction is stopped by the addition of 50 μl 0.3M sulphuric acid. The OD at 490 nm of the solution in each well is recorded. To quantitate the level of soluble OP-1 in the sample, a standard curve is performed in parallel with the test samples. In the standard curve, known increasing amounts of purified OP-1-pro is added. Alternatively, using, for example, Lumi-phos 530 (Analytical Luminescence Laboratories) as the substrate and detection at 300–650 nm in a standard luminometer, complexes can be detected by chemiluminescence, which typically provides a more sensitive assay than detection by means of a visible color change.

3b. Plate-based Radioimmunoassay

Osteogenic protein (soluble or mature form) may be detected in a standard plated-based radioimmunoassay as follows. Empirically determined limiting levels of anti-osteogenic protein antibody (e.g., anti-OP-1, typically 50–80 ng/well) are bound to wells of a PVC plate e.g., in 50 μl PBS phosphate buffered saline. After sufficient incubation to allow binding at room temperature, typically one hour, the plate is washed in a borate-buffered saline/Tween 20 solution, ("washing buffer"), and 200 μl of block (3% BSA, 0.1M lysine in 1×BSB) is added to each well and allowed to incubate for 1 hour, after which the wells are washed again in washing buffer. 40 μl of a sample composed of serially diluted plasma (preferably partially purified as described above) or osteogenic protein standard (e.g., OP-1) is added to wells in triplicate. Samples preferably are diluted in PTTH (15 mM $KH_2PO_4$, 8 mM $Na_2PO_4$, 27 mM KCl, 137 mM NaCl, 0.05% Tween 20, 1 mg/ml HSA, 0.05% $NaN_3$, pH 7.2). 10 μl of labelled competitor antigen, preferably 100,000–500,000 cpm/sample is added (e.g., $^{125}I$ OP-1, radiolabelled using standard procedures), and plates are incubated overnight at 4° C. Plates then are washed in washing buffer, and allowed to dry. Wells are cut apart and bound labelled OP-1 counted in a standard gamma counter. The quantities of bound labelled antigen (e.g., $^{125}I$ OP-1) measured in the presence and absence of sample then are compared, the difference being proportional to the amount of sample antigen (osteogenic protein) present in the sample fluid.

3c. Production Monitoring Considerations

Samples for testing the level of protein production includes culture supernatants or cell lysates, collected periodically and evaluated for OP-1 production by immunoblot analysis (Sambrook et al., eds., 1989, *Molecular Cloning*, Cold Spring Harbor Press, Cold Spring Harbor, N.Y.), or a portion of the cell culture itself, collected periodically and used to prepare polyA+ RNA for mRNA analysis. To monitor de novo OP-1 synthesis, some cultures are labeled according to conventional procedures with an $^{35}S$-methionine/$^{35}S$-cysteine mixture for 6–24 hours and then evaluated to OP-1 synthesis by conventional immunoprecipitation methods.

3.d Diagnostics using Antibodies to Soluble Osteogenic Protein Complex

The antibodies of this invention also may be used to monitor the level of soluble protein in the body. Fluctuations in osteogenic protein levels present in the bloodstream or peritoneal fluid then may be used to evaluate tissue viability. For example, osteogenic proteins are detected associated with regenerating tissue and/or may be released from dying cells into surrounding peritoneal fluid.

Serum samples may be obtained by standard venipuncture and serum prepared by centrifugation at 3,000 RPM for ten minutes. Similarly, peritoneal fluid samples may be obtained by a standard fluid extraction methodology. The presence of osteogenic protein in the serum or peritoneal fluid then may be assessed by standard Western blot (immunoblot), ELISA or RIA procedures. Briefly, for example, with the ELISA, samples may be diluted in an appropriate buffer, such as phosphate-buffered saline, and 50 μl aliquots allowed to absorb to flat bottomed wells in microtitre plates pre-coated with soluble osteogenic protein-specific antibody, and allowed to incubate for 18 hours at 4° C. Plates then may be washed with a standard buffer and incubated with 50 μl aliquots of a second osteogenic protein-specific antibody conjugated with a detecting agent, e.g., biotin, in an appropriate buffer, for 90 minutes at room temperature. Osteogenic protein-antibody complexes then may be detected using standard procedures.

Alternatively, an osteogenic protein-specific affinity column may be created using, for example, soluble osteogenic protein-specific antibodies adsorbed to a column matrix, and passing the fluid sample through the matrix to selectively extract the protein of interest. The protein then is eluted. A suitable elution buffer may be determined empirically by determining appropriate binding and elution conditions first with a control (e.g., purified, recombinantly-produced protein.) Fractions then are tested for the presence of the soluble form protein by standard immunoblot. Protein concentrations in serum or other fluid samples then may be determined using standard protein quantification techniques, including by spectrophotometric absorbance or by quantitation by ELISA or RIA antibody assays. Using this procedure, OP-1 has been identified in serum.

OP-1 was detected in human serum using the following assay. A monoclonal antibody raised against mammalian, recombinantly produced OP-1 using standard immunology techniques well described in the art and described generally herein, was immobilized by passing the antibody over an activated agarose gel (e.g., Affi-Gel™, from Bio-Rad Laboratories, Richmond, Calif., prepared following manufacturer's instructions), and used to purify OP-1 from serum. Human serum then was passed over the column and eluted with 3M K-thiocyanate. K-thiocyanante fractions then were dialyzed in 6M urea, 20 mM $PO_4$, pH 7.0, applied to a C8 HPLC column, and eluted with a 20 minute, 25–50% acetonitrile/0.1% TFA gradient. Mature, recombinantly produced OP-1 homodimers elute between 20–22 minutes. Accordingly, these fractions from the affinity-purified human serum sample were collected and tested for the presence of OP-1 by standard immunoblot using an OP-1-specifc antibody, and the protein identity confirmed by N-terminal sequencing.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

---

What is claimed is:

1. An isolated binding partner having specific binding affinity for an epitope on a soluble complex form of an osteogenic protein, said soluble complex form being characterized as a dimeric protein comprising a pair of polypeptide chain subunits associated to define a dimeric structure capable of inducing endochondral bone formation in a mammal when implanted in said mammal in association with a matrix, each said subunit having less than 200 amino acids, at least one of said subunits being non-covalently complexed with a peptide comprising a pro domain of a precursor form of an osteogenic protein subunit, or an allelic, species or sequence variant thereof, to form a complex which is more soluble in aqueous solvents than the uncomplexed pair of subunits, said binding partner being further characterized as having substantially no binding affinity for the mature, dimeric form of said osteogenic protein or a said pro domain of a precursor of one of said subunits.

2. The binding partner of claim 1 wherein said binding partner is an antibody.

3. The antibody of claim 2 wherein said antibody is a monoclonal antibody.

4. The antibody of claim 2 wherein said antibody is a polyclonal antibody.

5. The binding partner of claim 1 wherein one said subunit of said dimeric osteogenic protein is an OP1 polypeptide chain including allelic, species and sequence varients thereof.

6. The binding partner of claim 5 wherein the other subunit of said dimeric osteogenic protein is selected from the group consisting of OP1, BMP2, BMP3 or BMP4, including allelic, species and sequence variants thereof.

7. The binding partner of claim 5 wherein the other subunit of said dimeric osteogenic protein is selected from the group consisting of OP2, BMP5, BMP6 or BMP9, including allelic, species and sequence variants thereof.

8. The binding partner of claim 5 wherein the other subunit of said dimeric osteogenic protein is selected from the group consisting of DPP, 60A, Vgl, Vgr-1, including allelic, species and sequence variants thereof.

9. The isolated binding partner of claim 1 wherein said peptide comprises at least the first 18 amino acids of an amino acid sequence defining said pro domain.

10. The isolated binding partner of claim 9 wherein said peptide comprises the full length form of said pro domain.

11. The binding partner of claim 1 wherein the pro domain peptide non-covalently associated with said dimeric protein species comprises an amino acid sequence selected from the group consisting of OP1, OP2, BMP2, BMP3, BMP4, BMP5, BMP6, DPP, Vg1, Vgr-1, 60A, including allelic, species and sequence variants thereof.

12. The isolated binding partner of claim 1 wherein said osteogenic protein is a synthetic homolog of an osteogenic protein.

13. The isolated binding partner of claim 12 wherein said synthetic homolog is selected from the group consisting of COP 1, 3, 5, 7 and 16.

14. A method for specifically identifying a soluble complex form of an osteogenic protein in solution, wherein a binding partner has specific binding affinity for said soluble complex form, said soluble complex being characterized as a dimeric promin comprising a pair of protein subunits associated to define a dimeric structure capable of inducing endochondral bone formation in a mammal when implanted in said mammal in association with a matrix, each said subunit having less than about 200 amine acids; at least one of said subunits being noncovalenfly complexed with a peptide comprising a pro domain of a precursor form of an osteogeaic protein subunit, or an allelic, species, or sequence variant thereof, to form a soluble complex which is more soluble in aqueous solvents than the tmcomplexed pair of subunits, said binding partner being characterized as having binding affinity for said complexed form and said uncomplexed dimeric form but not said pro domain of a precursor form of one of said subunits, said method comprising the steps of:

(a) exposing a solution likely to contain said soluble complex to a binding partner having specific binding affinity for a said soluble complex under conditions to promote specific binding between said soluble complex and said binding partner to form a complex, and (b) detecting the complex formed.

15. The method of claim 14 wherein said binding partner is an antibody.

16. The method of claim 15 wherein said antibody is a monoclonal antibody.

17. The method of claim 15 wherein said antibody is a polyclonal antibody.

18. The method of claim 14 wherein said binding partner comprises a detection means.

19. The method of claim 18 wherein said detection means comprises an enzyme or radioactive atom.

20. The method of claim 14 wherein said soluble complex is detected by means of a second binding partner having specificity for said soluble complex.

21. The method of claim 14 wherein said soluble complex is present in admixture with other forms of osteogenic protein.

22. The method of claim 14 comprising the additional step of quantitating the amount of soluble complex formed.

23. The method of claim 14 wherein said solution in step (a) is exposed to a first immobilized binding partner having specificity for said soluble complex form under conditions sufficient to promote specific binding interaction between said first binding partner and said soluble complex form to form a soluble complex, and said step of detecting (b) comprises the step of exposing said soluble complex to a second binding partner having binding specificity for one of the proteins in said soluble complex.

24. The method of claim 23 wherein said second binding partner has specific binding affinity for said soluble complex form of said osteogenic protein.

25. The method according to claim 14 wherein said binding partner has a specific affinity for a soluble complex form of an osteogenic protein selected from the group consisting of OP1, OP2, BMP2, BMP3, BMP4, BMP5, BMP6, DPP, Vgl, Vgr-1, 60A, and allclic, species, or sequence variants thereof.

26. A kit for detecting a soluble complex form of an osteogenically active promin in solution, wherein a binding partner has specific binding affinity for said soluble complex form, said soluble complex being characterized as a dimeric protein comprising a pair of protein subunits associated to define a dimeric structure capable of inducing endochondral bone formation in a mammal when implanted in said mammal in association with a matrix, each said subunit having less than about 200 amino acids; at least one of said subunits being noncovalently complexed with a peptide comprising a pro domain of a precursor form of an osteogenic protein subunit, or an allelic, species, or sequence variant thereof, to form a soluble complex which is more soluble in aqueous solvents than the uncomplexed pair of subunits, said binding partner being characterized as having binding affinity for said complexed form and said uncomplexed, dimeric form but not said pro domain of a precursor form of one of said subunits, the kit comprising:

(a) means for capturing a fluid sample comprising osteogenic protein, (b) a binding partner having specific binding affinity for a said soluble complex form of said osteogenic protein, and (c) means for detecting said binding partner bound to said soluble complex form.

27. The kit of claim 26 wherein said binding partner is an antibody.

28. The kit of claim 26 wherein said fluid sample is a culture medium.

29. The kit of claim 26 wherein said means for detecting (c) comprises a second binding partner having specific binding affinity for said soluble complex form of said osteogenic protein.

30. The kit of claim 26 wherein said binding partner has a specific affinity for a soluble complex form of an osteogenic protein selected from the group consisting of OP1, OP2, BMP2, BMP3, BMP4, BMP5, BMP6, DPP, Vgl, Vgr-1, 60A, and allelic, species, or sequence variants thereof.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1822 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO ( i v ) ANTI-SENSE: NO ( v i ) ORIGINAL SOURCE:
 ( A ) ORGANISM: HOMO SAPIENS
 ( F ) TISSUE TYPE: HIPPOCAMPUS ( i x ) FEATURE:
 ( A ) NAME/KEY: CDS
 ( B ) LOCATION: 49..1341
 ( C ) IDENTIFICATION METHOD: experimental
 ( D ) OTHER INFORMATION: /function= "OSTEOGENIC PROTEIN"
  / product= "OP1"
  / evidence= EXPERIMENTAL
  / standard_name= "OP1"

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| GGTGCGGGCC | CGGAGCCCGG | AGCCCGGGTA | GCGCGTAGAG | CCGGCGCG | ATG | CAC | GTG | | | | | | | | | 57 |
| | | | | | Met | His | Val | | | | | | | | | |
| | | | | | 1 | | | | | | | | | | | |
| CGC | TCA | CTG | CGA | GCT | GCG | GCG | CCG | CAC | AGC | TTC | GTG | GCG | CTC | TGG | GCA | 105 |
| Arg | Ser | Leu | Arg | Ala | Ala | Ala | Pro | His | Ser | Phe | Val | Ala | Leu | Trp | Ala | |
| | 5 | | | | 10 | | | | | 15 | | | | | | |
| CCC | CTG | TTC | CTG | CTG | CGC | TCC | GCC | CTG | GCC | GAC | TTC | AGC | CTG | GAC | AAC | 153 |
| Pro | Leu | Phe | Leu | Leu | Arg | Ser | Ala | Leu | Ala | Asp | Phe | Ser | Leu | Asp | Asn | |
| 20 | | | | | 25 | | | | | 30 | | | | | 35 | |
| GAG | GTG | CAC | TCG | AGC | TTC | ATC | CAC | CGG | CGC | CTC | CGC | AGC | CAG | GAG | CGG | 201 |
| Glu | Val | His | Ser | Ser | Phe | Ile | His | Arg | Arg | Leu | Arg | Ser | Gln | Glu | Arg | |
| | | | | 40 | | | | | 45 | | | | | 50 | | |
| CGG | GAG | ATG | CAG | CGC | GAG | ATC | CTC | TCC | ATT | TTG | GGC | TTG | CCC | CAC | CGC | 249 |
| Arg | Glu | Met | Gln | Arg | Glu | Ile | Leu | Ser | Ile | Leu | Gly | Leu | Pro | His | Arg | |
| | | | 55 | | | | | 60 | | | | | 65 | | | |
| CCG | CGC | CCG | CAC | CTC | CAG | GGC | AAG | CAC | AAC | TCG | GCA | CCC | ATG | TTC | ATG | 297 |
| Pro | Arg | Pro | His | Leu | Gln | Gly | Lys | His | Asn | Ser | Ala | Pro | Met | Phe | Met | |
| | | 70 | | | | | 75 | | | | | 80 | | | | |
| CTG | GAC | CTG | TAC | AAC | GCC | ATG | GCG | GTG | GAG | GAG | GGC | GGC | GGG | CCC | GGC | 345 |
| Leu | Asp | Leu | Tyr | Asn | Ala | Met | Ala | Val | Glu | Glu | Gly | Gly | Gly | Pro | Gly | |
| | 85 | | | | | 90 | | | | | 95 | | | | | |
| GGC | CAG | GGC | TTC | TCC | TAC | CCC | TAC | AAG | GCC | GTC | TTC | AGT | ACC | CAG | GGC | 393 |
| Gly | Gln | Gly | Phe | Ser | Tyr | Pro | Tyr | Lys | Ala | Val | Phe | Ser | Thr | Gln | Gly | |
| 100 | | | | | 105 | | | | | 110 | | | | | 115 | |
| CCC | CCT | CTG | GCC | AGC | CTG | CAA | GAT | AGC | CAT | TTC | CTC | ACC | GAC | GCC | GAC | 441 |
| Pro | Pro | Leu | Ala | Ser | Leu | Gln | Asp | Ser | His | Phe | Leu | Thr | Asp | Ala | Asp | |
| | | | | 120 | | | | | 125 | | | | | 130 | | |
| ATG | GTC | ATG | AGC | TTC | GTC | AAC | CTC | GTG | GAA | CAT | GAC | AAG | GAA | TTC | TTC | 489 |
| Met | Val | Met | Ser | Phe | Val | Asn | Leu | Val | Glu | His | Asp | Lys | Glu | Phe | Phe | |
| | | | 135 | | | | | 140 | | | | | 145 | | | |
| CAC | CCA | CGC | TAC | CAC | CAT | CGA | GAG | TTC | CGG | TTT | GAT | CTT | TCC | AAG | ATC | 537 |
| His | Pro | Arg | Tyr | His | His | Arg | Glu | Phe | Arg | Phe | Asp | Leu | Ser | Lys | Ile | |
| | | 150 | | | | | 155 | | | | | 160 | | | | |
| CCA | GAA | GGG | GAA | GCT | GTC | ACG | GCA | GCC | GAA | TTC | CGG | ATC | TAC | AAG | GAC | 585 |
| Pro | Glu | Gly | Glu | Ala | Val | Thr | Ala | Ala | Glu | Phe | Arg | Ile | Tyr | Lys | Asp | |
| | 165 | | | | | 170 | | | | | 175 | | | | | |
| TAC | ATC | CGG | GAA | CGC | TTC | GAC | AAT | GAG | ACG | TTC | CGG | ATC | AGC | GTT | TAT | 633 |
| Tyr | Ile | Arg | Glu | Arg | Phe | Asp | Asn | Glu | Thr | Phe | Arg | Ile | Ser | Val | Tyr | |
| 180 | | | | | 185 | | | | | 190 | | | | | 195 | |
| CAG | GTG | CTC | CAG | GAG | CAC | TTG | GGC | AGG | GAA | TCG | GAT | CTC | TTC | CTG | CTC | 681 |
| Gln | Val | Leu | Gln | Glu | His | Leu | Gly | Arg | Glu | Ser | Asp | Leu | Phe | Leu | Leu | |
| | | | | 200 | | | | | 205 | | | | | 210 | | |
| GAC | AGC | CGT | ACC | CTC | TGG | GCC | TCG | GAG | GAG | GGC | TGG | CTG | GTG | TTT | GAC | 729 |
| Asp | Ser | Arg | Thr | Leu | Trp | Ala | Ser | Glu | Glu | Gly | Trp | Leu | Val | Phe | Asp | |
| | | | 215 | | | | | 220 | | | | | 225 | | | |
| ATC | ACA | GCC | ACC | AGC | AAC | CAC | TGG | GTG | GTC | AAT | CCG | CGG | CAC | AAC | CTG | 777 |
| Ile | Thr | Ala | Thr | Ser | Asn | His | Trp | Val | Val | Asn | Pro | Arg | His | Asn | Leu | |
| | | 230 | | | | | 235 | | | | | 240 | | | | |

| | | | | | | | | | | | | | | | | |
|---|---|---|---|---|---|---|---|---|---|---|---|---|---|---|---|---|
| GGC | CTG | CAG | CTC | TCG | GTG | GAG | ACG | CTG | GAT | GGG | CAG | AGC | ATC | AAC | CCC | 825 |
| Gly | Leu | Gln | Leu | Ser | Val | Glu | Thr | Leu | Asp | Gly | Gln | Ser | Ile | Asn | Pro | |
| | 245 | | | | 250 | | | | | | 255 | | | | | |
| AAG | TTG | GCG | GGC | CTG | ATT | GGG | CGG | CAC | GGG | CCC | CAG | AAC | AAG | CAG | CCC | 873 |
| Lys | Leu | Ala | Gly | Leu | Ile | Gly | Arg | His | Gly | Pro | Gln | Asn | Lys | Gln | Pro | |
| 260 | | | | | 265 | | | | | 270 | | | | | 275 | |
| TTC | ATG | GTG | GCT | TTC | TTC | AAG | GCC | ACG | GAG | GTC | CAC | TTC | CGC | AGC | ATC | 921 |
| Phe | Met | Val | Ala | Phe | Phe | Lys | Ala | Thr | Glu | Val | His | Phe | Arg | Ser | Ile | |
| | | | | 280 | | | | | 285 | | | | | 290 | | |
| CGG | TCC | ACG | GGG | AGC | AAA | CAG | CGC | AGC | CAG | AAC | CGC | TCC | AAG | ACG | CCC | 969 |
| Arg | Ser | Thr | Gly | Ser | Lys | Gln | Arg | Ser | Gln | Asn | Arg | Ser | Lys | Thr | Pro | |
| | | | 295 | | | | 300 | | | | | 305 | | | | |
| AAG | AAC | CAG | GAA | GCC | CTG | CGG | ATG | GCC | AAC | GTG | GCA | GAG | AAC | AGC | AGC | 1017 |
| Lys | Asn | Gln | Glu | Ala | Leu | Arg | Met | Ala | Asn | Val | Ala | Glu | Asn | Ser | Ser | |
| | | 310 | | | | | 315 | | | | | 320 | | | | |
| AGC | GAC | CAG | AGG | CAG | GCC | TGT | AAG | AAG | CAC | GAG | CTG | TAT | GTC | AGC | TTC | 1065 |
| Ser | Asp | Gln | Arg | Gln | Ala | Cys | Lys | Lys | His | Glu | Leu | Tyr | Val | Ser | Phe | |
| | 325 | | | | | 330 | | | | | 335 | | | | | |
| CGA | GAC | CTG | GGC | TGG | CAG | GAC | TGG | ATC | ATC | GCG | CCT | GAA | GGC | TAC | GCC | 1113 |
| Arg | Asp | Leu | Gly | Trp | Gln | Asp | Trp | Ile | Ile | Ala | Pro | Glu | Gly | Tyr | Ala | |
| 340 | | | | | 345 | | | | | 350 | | | | | 355 | |
| GCC | TAC | TAC | TGT | GAG | GGG | GAG | TGT | GCC | TTC | CCT | CTG | AAC | TCC | TAC | ATG | 1161 |
| Ala | Tyr | Tyr | Cys | Glu | Gly | Glu | Cys | Ala | Phe | Pro | Leu | Asn | Ser | Tyr | Met | |
| | | | | 360 | | | | | 365 | | | | | 370 | | |
| AAC | GCC | ACC | AAC | CAC | GCC | ATC | GTG | CAG | ACG | CTG | GTC | CAC | TTC | ATC | AAC | 1209 |
| Asn | Ala | Thr | Asn | His | Ala | Ile | Val | Gln | Thr | Leu | Val | His | Phe | Ile | Asn | |
| | | | 375 | | | | 380 | | | | | 385 | | | | |
| CCG | GAA | ACG | GTG | CCC | AAG | CCC | TGC | TGT | GCG | CCC | ACG | CAG | CTC | AAT | GCC | 1257 |
| Pro | Glu | Thr | Val | Pro | Lys | Pro | Cys | Cys | Ala | Pro | Thr | Gln | Leu | Asn | Ala | |
| | | 390 | | | | | 395 | | | | | 400 | | | | |
| ATC | TCC | GTC | CTC | TAC | TTC | GAT | GAC | AGC | TCC | AAC | GTC | ATC | CTG | AAG | AAA | 1305 |
| Ile | Ser | Val | Leu | Tyr | Phe | Asp | Asp | Ser | Ser | Asn | Val | Ile | Leu | Lys | Lys | |
| | 405 | | | | | 410 | | | | | 415 | | | | | |
| TAC | AGA | AAC | ATG | GTG | GTC | CGG | GCC | TGT | GGC | TGC | CAC | TAGCTCCTCC | | | | 1351 |
| Tyr | Arg | Asn | Met | Val | Val | Arg | Ala | Cys | Gly | Cys | His | | | | | |
| 420 | | | | | 425 | | | | | 430 | | | | | | |

```
GAGAATTCAG ACCCTTTGGG GCCAAGTTTT TCTGGATCCT CCATTGCTCG CCTTGGCCAG        1411

GAACCAGCAG ACCAACTGCC TTTTGTGAGA CCTTCCCCTC CCTATCCCCA ACTTTAAAGG        1471

TGTGAGAGTA TTAGGAAACA TGAGCAGCAT ATGGCTTTTG ATCAGTTTTT CAGTGGCAGC        1531

ATCCAATGAA CAAGATCCTA CAAGCTGTGC AGGCAAAACC TAGCAGGAAA AAAAAACAAC        1591

GCATAAAGAA AAATGGCCGG GCCAGGTCAT TGGCTGGGAA GTCTCAGCCA TGCACGGACT        1651

CGTTTCCAGA GGTAATTATG AGCGCCTACC AGCCAGGCCA CCCAGCCGTG GGAGGAAGGG        1711

GGCGTGGCAA GGGGTGGGCA CATTGGTGTC TGTGCGAAAG GAAAATTGAC CCGGAAGTTC        1771

CTGTAATAAA TGTCACAATA AAACGAATGA ATGAAAAAAA AAAAAAAAA A                 1822
```

( 2 ) INFORMATION FOR SEQ ID NO:2:

( i ) SEQUENCE CHARACTERISTICS:
            ( A ) LENGTH: 431 amino acids
            ( B ) TYPE: amino acid
            ( D ) TOPOLOGY: linear        ( i i ) MOLECULE TYPE: protein        ( x i ) SEQUENCE DESCRIPTION: SEQ ID NO:2:

| Met | His | Val | Arg | Ser | Leu | Arg | Ala | Ala | Ala | Pro | His | Ser | Phe | Val | Ala |
|---|---|---|---|---|---|---|---|---|---|---|---|---|---|---|---|
| 1 | | | | 5 | | | | | 10 | | | | | 15 | |

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100             105             110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
    275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

( 2 ) INFORMATION FOR SEQ ID NO:3:

( i ) SEQUENCE CHARACTERISTICS:
  ( A ) LENGTH: 1723 base pairs
  ( B ) TYPE: nucleic acid
  ( C ) STRANDEDNESS: single
  ( D ) TOPOLOGY: linear ( i i ) MOLECULE TYPE: cDNA ( v i ) ORIGINAL SOURCE:
  ( A ) ORGANISM: Homo sapiens
  ( F ) TISSUE TYPE: HIPPOCAMPUS ( i x ) FEATURE:
  ( A ) NAME/KEY: CDS
  ( B ) LOCATION: 490..1696
  ( D ) OTHER INFORMATION: /function= "OSTEOGENIC PROTEIN"
    / product= "hOP2-PP"
    / note= "hOP2 (cDNA)"

( x i ) SEQUENCE DESCRIPTION: SEQ ID NO:3:

```
GGCGCCGGCA  GAGCAGGAGT  GGCTGGAGGA  GCTGTGGTTG  GAGCAGGAGG  TGGCACGGCA      60

GGGCTGGAGG  GCTCCCTATG  AGTGGCGGAG  ACGGCCCAGG  AGGCGCTGGA  GCAACAGCTC     120

CCACACCGCA  CCAAGCGGTG  GCTGCAGGAG  CTCGCCCATC  GCCCCTGCGC  TGCTCGGACC     180

GCGGCCACAG  CCGGACTGGC  GGGTACGGCG  GCGACAGAGG  CATTGGCCGA  GAGTCCCAGT     240

CCGCAGAGTA  GCCCCGGCCT  CGAGGCGGTG  GCGTCCCGGT  CCTCTCCGTC  CAGGAGCCAG     300

GACAGGTGTC  GCGCGGCGGG  GCTCCAGGGA  CCGCGCCTGA  GGCCGGCTGC  CCGCCCGTCC     360

CGCCCCGCCC  CGCCGCCCGC  CGCCCGCCGA  GCCCAGCCTC  CTTGCCGTCG  GGGCGTCCCC     420

AGGCCCTGGG  TCGGCCGCGG  AGCCGATGCG  CGCCCGCTGA  GCGCCCAGC  TGAGCGCCCC      480
```

| CGGCCTGCC | ATG<br>Met<br>1 | ACC<br>Thr | GCG<br>Ala | CTC<br>Leu | CCC<br>Pro<br>5 | GGC<br>Gly | CCG<br>Pro | CTC<br>Leu | TGG<br>Trp | CTC<br>Leu<br>10 | CTG<br>Leu | GGC<br>Gly | CTG<br>Leu | 528 |
|---|---|---|---|---|---|---|---|---|---|---|---|---|---|---|
| GCG<br>Ala | CTA<br>Leu<br>15 | TGC<br>Cys | GCG<br>Ala | CTG<br>Leu | GGC<br>Gly | GGG<br>Gly<br>20 | GGC<br>Gly | GGC<br>Gly | CCC<br>Pro | GGC<br>Gly | CTG<br>Leu<br>25 | CGA<br>Arg | CCC<br>Pro | CCG<br>Pro | CCC<br>Pro | 576 |
| GGC<br>Gly<br>30 | TGT<br>Cys | CCC<br>Pro | CAG<br>Gln | CGA<br>Arg | CGT<br>Arg<br>35 | CTG<br>Leu | GGC<br>Gly | GCG<br>Ala | CGC<br>Arg | GAG<br>Glu<br>40 | CGC<br>Arg | CGG<br>Arg | GAC<br>Asp | GTG<br>Val | CAG<br>Gln<br>45 | 624 |
| CGC<br>Arg | GAG<br>Glu | ATC<br>Ile | CTG<br>Leu | GCG<br>Ala<br>50 | GTG<br>Val | CTC<br>Leu | GGG<br>Gly | CTG<br>Leu | CCT<br>Pro<br>55 | GGG<br>Gly | CGG<br>Arg | CCC<br>Pro | CGG<br>Arg | CCC<br>Pro<br>60 | CGC<br>Arg | 672 |
| GCG<br>Ala | CCA<br>Pro | CCC<br>Pro | GCC<br>Ala | GCC<br>Ala<br>65 | TCC<br>Ser | CGG<br>Arg | CTG<br>Leu | CCC<br>Pro<br>70 | GCG<br>Ala | TCC<br>Ser | GCG<br>Ala | CCG<br>Pro | CTC<br>Leu<br>75 | TTC<br>Phe | ATG<br>Met | 720 |
| CTG<br>Leu | GAC<br>Asp | CTG<br>Leu<br>80 | TAC<br>Tyr | CAC<br>His | GCC<br>Ala | ATG<br>Met | GCC<br>Ala<br>85 | GGC<br>Gly | GAC<br>Asp | GAC<br>Asp | GAC<br>Asp | GAG<br>Glu<br>90 | GAC<br>Asp | GGC<br>Gly | GCG<br>Ala | 768 |
| CCC<br>Pro | GCG<br>Ala<br>95 | GAG<br>Glu | CGG<br>Arg | CGC<br>Arg | CTG<br>Leu | GGC<br>Gly<br>100 | CGC<br>Arg | GCC<br>Ala | GAC<br>Asp | CTG<br>Leu | GTC<br>Val<br>105 | ATG<br>Met | AGC<br>Ser | TTC<br>Phe | GTT<br>Val | 816 |
| AAC<br>Asn | ATG<br>Met<br>110 | GTG<br>Val | GAG<br>Glu | CGA<br>Arg | GAC<br>Asp<br>115 | CGT<br>Arg | GCC<br>Ala | CTG<br>Leu | GGC<br>Gly | CAC<br>His<br>120 | CAG<br>Gln | GAG<br>Glu | CCC<br>Pro | CAT<br>His | TGG<br>Trp<br>125 | 864 |
| AAG<br>Lys | GAG<br>Glu | TTC<br>Phe | CGC<br>Arg | TTT<br>Phe<br>130 | GAC<br>Asp | CTG<br>Leu | ACC<br>Thr | CAG<br>Gln | ATC<br>Ile<br>135 | CCG<br>Pro | GCT<br>Ala | GGG<br>Gly | GAG<br>Glu | GCG<br>Ala<br>140 | GTC<br>Val | 912 |
| ACA<br>Thr | GCT<br>Ala | GCG<br>Ala | GAG<br>Glu | TTC<br>Phe<br>145 | CGG<br>Arg | ATT<br>Ile | TAC<br>Tyr | AAG<br>Lys | GTG<br>Val<br>150 | CCC<br>Pro | AGC<br>Ser | ATC<br>Ile | CAC<br>His | CTG<br>Leu<br>155 | CTC<br>Leu | 960 |
| AAC<br>Asn | AGG<br>Arg | ACC<br>Thr | CTC<br>Leu | CAC<br>His | GTC<br>Val | AGC<br>Ser | ATG<br>Met | TTC<br>Phe | CAG<br>Gln | GTG<br>Val | GTC<br>Val | CAG<br>Gln | GAG<br>Glu | CAG<br>Gln | TCC<br>Ser | 1008 |

|  |  |  |  |  | 160 |  |  |  |  | 165 |  |  |  |  | 170 |  |  |
|---|---|---|---|---|---|---|---|---|---|---|---|---|---|---|---|---|---|
| AAC | AGG | GAG | TCT | GAC | TTG | TTC | TTT | TTG | GAT | CTT | CAG | ACG | CTC | CGA | GCT | | 1056 |
| Asn | Arg | Glu | Ser | Asp | Leu | Phe | Phe | Leu | Asp | Leu | Gln | Thr | Leu | Arg | Ala | | |
| | 175 | | | | 180 | | | | | 185 | | | | | | | |
| GGA | GAC | GAG | GGC | TGG | CTG | GTG | CTG | GAT | GTC | ACA | GCA | GCC | AGT | GAC | TGC | | 1104 |
| Gly | Asp | Glu | Gly | Trp | Leu | Val | Leu | Asp | Val | Thr | Ala | Ala | Ser | Asp | Cys | | |
| 190 | | | | | 195 | | | | | 200 | | | | | 205 | | |
| TGG | TTG | CTG | AAG | CGT | CAC | AAG | GAC | CTG | GGA | CTC | CGC | CTC | TAT | GTG | GAG | | 1152 |
| Trp | Leu | Leu | Lys | Arg | His | Lys | Asp | Leu | Gly | Leu | Arg | Leu | Tyr | Val | Glu | | |
| | | | | 210 | | | | | 215 | | | | | 220 | | | |
| ACT | GAG | GAC | GGG | CAC | AGC | GTG | GAT | CCT | GGC | CTG | GCC | GGC | CTG | CTG | GGT | | 1200 |
| Thr | Glu | Asp | Gly | His | Ser | Val | Asp | Pro | Gly | Leu | Ala | Gly | Leu | Leu | Gly | | |
| | | | 225 | | | | | 230 | | | | | 235 | | | | |
| CAA | CGG | GCC | CCA | CGC | TCC | CAA | CAG | CCT | TTC | GTG | GTC | ACT | TTC | TTC | AGG | | 1248 |
| Gln | Arg | Ala | Pro | Arg | Ser | Gln | Gln | Pro | Phe | Val | Val | Thr | Phe | Phe | Arg | | |
| | | 240 | | | | | 245 | | | | | 250 | | | | | |
| GCC | AGT | CCG | AGT | CCC | ATC | CGC | ACC | CCT | CGG | GCA | GTG | AGG | CCA | CTG | AGG | | 1296 |
| Ala | Ser | Pro | Ser | Pro | Ile | Arg | Thr | Pro | Arg | Ala | Val | Arg | Pro | Leu | Arg | | |
| | 255 | | | | | 260 | | | | | 265 | | | | | | |
| AGG | AGG | CAG | CCG | AAG | AAA | AGC | AAC | GAG | CTG | CCG | CAG | GCC | AAC | CGA | CTC | | 1344 |
| Arg | Arg | Gln | Pro | Lys | Lys | Ser | Asn | Glu | Leu | Pro | Gln | Ala | Asn | Arg | Leu | | |
| 270 | | | | | 275 | | | | | 280 | | | | | 285 | | |
| CCA | GGG | ATC | TTT | GAT | GAC | GTC | CAC | GGC | TCC | CAC | GGC | CGG | CAG | GTC | TGC | | 1392 |
| Pro | Gly | Ile | Phe | Asp | Asp | Val | His | Gly | Ser | His | Gly | Arg | Gln | Val | Cys | | |
| | | | | 290 | | | | | 295 | | | | | 300 | | | |
| CGT | CGG | CAC | GAG | CTC | TAC | GTC | AGC | TTC | CAG | GAC | CTC | GGC | TGG | CTG | GAC | | 1440 |
| Arg | Arg | His | Glu | Leu | Tyr | Val | Ser | Phe | Gln | Asp | Leu | Gly | Trp | Leu | Asp | | |
| | | | 305 | | | | | 310 | | | | | 315 | | | | |
| TGG | GTC | ATC | GCT | CCC | CAA | GGC | TAC | TCG | GCC | TAT | TAC | TGT | GAG | GGG | GAG | | 1488 |
| Trp | Val | Ile | Ala | Pro | Gln | Gly | Tyr | Ser | Ala | Tyr | Tyr | Cys | Glu | Gly | Glu | | |
| | | 320 | | | | | 325 | | | | | 330 | | | | | |
| TGC | TCC | TTC | CCA | CTG | GAC | TCC | TGC | ATG | AAT | GCC | ACC | AAC | CAC | GCC | ATC | | 1536 |
| Cys | Ser | Phe | Pro | Leu | Asp | Ser | Cys | Met | Asn | Ala | Thr | Asn | His | Ala | Ile | | |
| | 335 | | | | | 340 | | | | | 345 | | | | | | |
| CTG | CAG | TCC | CTG | GTG | CAC | CTG | ATG | AAG | CCA | AAC | GCA | GTC | CCC | AAG | GCG | | 1584 |
| Leu | Gln | Ser | Leu | Val | His | Leu | Met | Lys | Pro | Asn | Ala | Val | Pro | Lys | Ala | | |
| 350 | | | | | 355 | | | | | 360 | | | | | 365 | | |
| TGC | TGT | GCA | CCC | ACC | AAG | CTG | AGC | GCC | ACC | TCT | GTG | CTC | TAC | TAT | GAC | | 1632 |
| Cys | Cys | Ala | Pro | Thr | Lys | Leu | Ser | Ala | Thr | Ser | Val | Leu | Tyr | Tyr | Asp | | |
| | | | | 370 | | | | | 375 | | | | | 380 | | | |
| AGC | AGC | AAC | AAC | GTC | ATC | CTG | CGC | AAA | GCC | CGC | AAC | ATG | GTG | GTC | AAG | | 1680 |
| Ser | Ser | Asn | Asn | Val | Ile | Leu | Arg | Lys | Ala | Arg | Asn | Met | Val | Val | Lys | | |
| | | | 385 | | | | | 390 | | | | | 395 | | | | |
| GCC | TGC | GGC | TGC | CAC | T | GAGTCAGCCC | GCCCAGCCCT | ACTGCAG | | | | | | | | | 1723 |
| Ala | Cys | Gly | Cys | His | | | | | | | | | | | | | |
| | | | | 400 | | | | | | | | | | | | | |

( 2 ) INFORMATION FOR SEQ ID NO:4:

( i ) SEQUENCE CHARACTERISTICS:
        ( A ) LENGTH: 402 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:4:

| Met | Thr | Ala | Leu | Pro | Gly | Pro | Leu | Trp | Leu | Leu | Gly | Leu | Ala | Leu | Cys |
|---|---|---|---|---|---|---|---|---|---|---|---|---|---|---|---|
| 1 | | | | 5 | | | | | 10 | | | | | 15 | |

| Ala | Leu | Gly | Gly | Gly | Gly | Pro | Gly | Leu | Arg | Pro | Pro | Gly | Cys | Pro |
|---|---|---|---|---|---|---|---|---|---|---|---|---|---|---|
| | | | 20 | | | | | 25 | | | | | 30 | |

```
Gln Arg Arg Leu Gly Ala Arg Glu Arg Arg Asp Val Gln Arg Glu Ile
         35                  40                  45

Leu Ala Val Leu Gly Leu Pro Gly Arg Pro Arg Pro Arg Ala Pro Pro
     50              55              60

Ala Ala Ser Arg Leu Pro Ala Ser Ala Pro Leu Phe Met Leu Asp Leu
65              70              75                           80

Tyr His Ala Met Ala Gly Asp Asp Asp Glu Asp Gly Ala Pro Ala Glu
             85                  90                  95

Arg Arg Leu Gly Arg Ala Asp Leu Val Met Ser Phe Val Asn Met Val
         100                 105                 110

Glu Arg Asp Arg Ala Leu Gly His Gln Glu Pro His Trp Lys Glu Phe
         115                 120             125

Arg Phe Asp Leu Thr Gln Ile Pro Ala Gly Glu Ala Val Thr Ala Ala
    130                 135                 140

Glu Phe Arg Ile Tyr Lys Val Pro Ser Ile His Leu Leu Asn Arg Thr
145             150                 155                     160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200             205

Lys Arg His Lys Asp Leu Gly Leu Arg Leu Tyr Val Glu Thr Glu Asp
    210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
            245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
    275                 280                 285

Phe Asp Asp Val His Gly Ser His Gly Arg Gln Val Cys Arg Arg His
290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
            325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
        355                 360                 365

Pro Thr Lys Leu Ser Ala Thr Ser Val Leu Tyr Tyr Asp Ser Ser Asn
    370                 375                 380

Asn Val Ile Leu Arg Lys Ala Arg Asn Met Val Val Lys Ala Cys Gly
385                 390                 395                 400

Cys His
```

( 2 ) INFORMATION FOR SEQ ID NO:5:

( i ) SEQUENCE CHARACTERISTICS:
( A ) LENGTH: 102 amino acids
( B ) TYPE: amino acid
( D ) TOPOLOGY: linear ( i i ) MOLECULE TYPE: protein ( i x ) FEATURE:
 ( A ) NAME/KEY: Protein
 ( B ) LOCATION: 1..102
 ( D ) OTHER INFORMATION: /label= OPX
 / note= "WHEREIN EACH XAA IS INDEPENDENTLY SELECTED FROM A GROUP OF ONE OR MORE SPECIFIED AMINO ACIDS AS DEFINED IN THE SPECIFICATION"

( x i ) SEQUENCE DESCRIPTION: SEQ ID NO:5:

| Cys | Xaa | Xaa | His | Glu | Leu | Tyr | Val | Xaa | Phe | Xaa | Asp | Leu | Gly | Trp | Xaa |
|---|---|---|---|---|---|---|---|---|---|---|---|---|---|---|---|
| 1 | | | | 5 | | | | | 10 | | | | | 15 | |
| Asp | Trp | Xaa | Ile | Ala | Pro | Xaa | Gly | Tyr | Xaa | Ala | Tyr | Tyr | Cys | Glu | Gly |
| | | | 20 | | | | 25 | | | | | | 30 | | |
| Glu | Cys | Xaa | Phe | Pro | Leu | Xaa | Ser | Xaa | Met | Asn | Ala | Thr | Asn | His | Ala |
| | | 35 | | | | 40 | | | | | | 45 | | | |
| Ile | Xaa | Gln | Xaa | Leu | Val | His | Xaa | Xaa | Xaa | Pro | Xaa | Xaa | Val | Pro | Lys |
| | 50 | | | | | 55 | | | | | 60 | | | | |
| Xaa | Cys | Cys | Ala | Pro | Thr | Xaa | Leu | Xaa | Ala | Xaa | Ser | Val | Leu | Tyr | Xaa |
| 65 | | | | | 70 | | | | | 75 | | | | | 80 |
| Asp | Xaa | Ser | Xaa | Asn | Val | Xaa | Leu | Xaa | Lys | Xaa | Arg | Asn | Met | Val | Val |
| | | | | 85 | | | | | 90 | | | | | 95 | |
| Xaa | Ala | Cys | Gly | Cys | His | | | | | | | | | | |
| | | | 100 | | | | | | | | | | | | |

( 2 ) INFORMATION FOR SEQ ID NO:6:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Cleavage-site
  ( B ) LOCATION: 1..4
  ( D ) OTHER INFORMATION: /note= "PROTEOLYTIC CLEAVAGE SITE"

( x i ) SEQUENCE DESCRIPTION: SEQ ID NO:6:

Arg  Xaa  Xaa  Arg
 1